(12) United States Patent
Kuehfuss

(10) Patent No.: US 8,221,331 B2
(45) Date of Patent: Jul. 17, 2012

(54) APPARATUS FOR FETAL SCALP BLOOD SAMPLING

(75) Inventor: Andreas Kuehfuss, Wurmlingen (DE)

(73) Assignee: Karl Storz GmbH & Co. KG (DE)

( * ) Notice: Subject to any disclaimer, the term of this patent is extended or adjusted under 35 U.S.C. 154(b) by 431 days.

(21) Appl. No.: 11/854,695

(22) Filed: Sep. 13, 2007

(65) Prior Publication Data

US 2008/0097245 A1 Apr. 24, 2008

(30) Foreign Application Priority Data

Sep. 13, 2006 (DE) .................. 10 2006 042 903

(51) Int. Cl.
*A61B 5/00* (2006.01)

(52) U.S. Cl. .......................... 600/583; 606/182
(58) Field of Classification Search .............. 600/583; 606/167, 182
See application file for complete search history.

(56) References Cited

U.S. PATENT DOCUMENTS

| | | | |
|---|---|---|---|
| 3,685,509 A | 8/1972 | Bental | 128/2 |
| 4,360,016 A * | 11/1982 | Sarrine | 600/576 |
| 4,503,856 A * | 3/1985 | Cornell et al. | 606/182 |
| 4,653,513 A | 3/1987 | Dombrowski | |
| 5,301,684 A * | 4/1994 | Ogirala | 600/567 |
| 5,336,176 A * | 8/1994 | Yoon | 604/506 |
| 5,908,432 A * | 6/1999 | Pan | 606/167 |
| 6,423,011 B1 | 7/2002 | Arulkumaran et al. | |
| 2004/0193197 A1 | 9/2004 | Vidal | 606/167 |

FOREIGN PATENT DOCUMENTS

| | | |
|---|---|---|
| DE | 84 21 169 | 4/1985 |
| WO | 2006043164 A1 | 4/2006 |

OTHER PUBLICATIONS

Definition of spring-loaded, dictionary.com, Dec. 8, 2009.*
European Search Report, EP07017929, Dec. 13, 2007, 8 pages.
German Search Report, May 30, 2007, 4 pages.
"Fetal Scalp Blood Sampler" Brenner Medical; http://www.pc-project.com/brenner-htm/brenner/fetal.html, 2 pages, May 10, 2004.

* cited by examiner

*Primary Examiner* — Max Hindenburg
*Assistant Examiner* — Renee Danega
(74) *Attorney, Agent, or Firm* — St. Onge Steward Johnston & Reens LLC

(57) ABSTRACT

The invention relates to an apparatus for fetal scalp blood sampling, having a shaft, a blade that is mounted removably in the distal end of the shaft and that can be slid by means of a positioning mechanism between a starting position mounted in the shaft and a working position extending beyond the distal end of the shaft, and also having a blood sampling device mounted on the distal end of the shaft. To create an apparatus for fetal scalp blood sampling that is easy to operate and also ensures a high degree of operating safety, it is proposed with the invention that the blade can be fixed by the positioning mechanism in the respective end position.

7 Claims, 4 Drawing Sheets

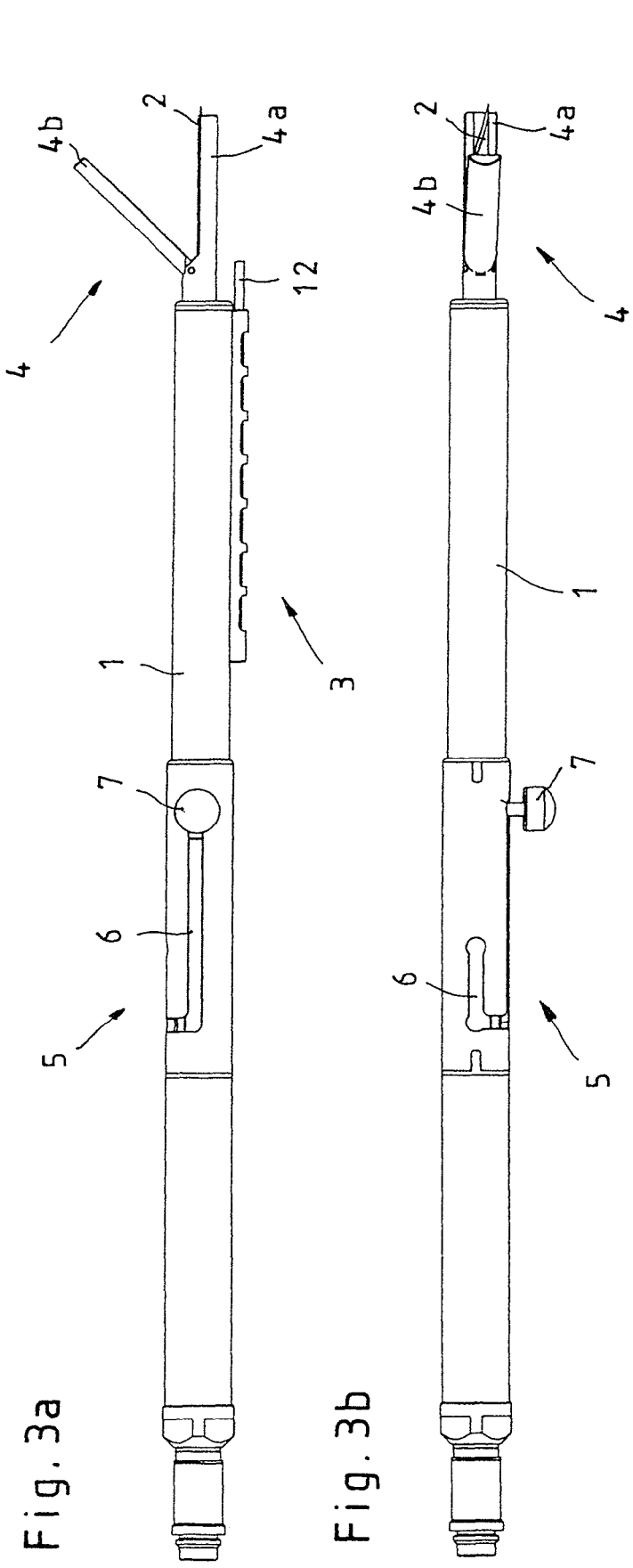

APPARATUS FOR FETAL SCALP BLOOD SAMPLING

CROSS-REFERENCE TO RELATED APPLICATIONS

The present application claims priority of German patent application No. 10 2006 042 903.6 filed on Sep. 13, 2006, the content of which is incorporated herein by reference.

FIELD OF THE INVENTION

The invention relates to an apparatus for fetal scalp blood sampling, having a shaft, a blade that is mounted removably in the distal end of the shaft and that can be slid by means of a positioning mechanism between a starting position mounted in the shaft and a working position extending beyond the distal end of the shaft, and also having a blood sampling device mounted on the distal end of the shaft.

BACKGROUND OF THE INVENTION

Fetal blood sampling has proven useful in the art, in particular to clarify pathological fetal heart frequency patterns during birth. It is possible, for instance, using the removal of blood samples, to determine the pH value, base-excess value, and other vital blood parameters easily and rapidly.

A generic apparatus with a blade that is removably mounted in the shaft is know, for instance, from DE 84 21 169 U1. In this known apparatus, the blade can be conveyed by means of a punch against the force of a return spring into the open working position. Because of the spring force of the return spring, the operator must hold the punch pressed together continuously throughout the period of use of the blade, restricting the convenience of using this apparatus.

An example of an additional apparatus for fetal blood sampling is the "Fetal Scalp Blood Sampler" of the Brenner Medical Firm, Putzbrunn. In this known apparatus, configured as a one-time instrument, the blade mounted slidably in the shaft constitutes a non-dissoluble firm component of the apparatus, so that it is not possible either to adjust to different incision depths of the blade or to reuse the apparatus after it is cleansed.

Consequently it is the object of the invention to create an apparatus for fetal blood removal that, along with ease of use, ensures a high degree of operating safety.

SUMMARY OF THE INVENTION

This object is fulfilled according to the invention in that the blade can be held in place in the respective end position by means of the positioning mechanism.

The blade, positioned in the blade holder, is slid by a positioning mechanism mounted in the shaft. To ensure that the blade remains, during use, in the respective desired end position, namely the starting position, working position, or change-over position, it is proposed with the invention that the blade should be fixable in the respective end position by means of the positioning mechanism.

It is further proposed with the invention that the positioning mechanism includes a push-button that can be pushed in a guide track, so that the contours of the guide track as well as of the bush-button shaft are attuned to one another in such a way that the push-button is positioned in the various end positions of the blade so that it cannot slide in the guide track.

Accidental actuation of the positioning mechanism can further be prevented, according to the invention, in that the push-button can be pressed against the force of at least one spring-elastic element into the guide track. This spring force working on the push-button thus prevents, on the one hand, any accidental sliding of the push-button by lateral blows and, on the other hand, ensures that the push-button is pre-tensed in the slide-proof end positions.

According to a preferred embodiment of the invention it is proposed that the blade should be mounted in a blade holder positioned so that it can slide in the shaft in the axial direction, and here it is possible to make use of basically familiar scalpel blades.

To prevent accidental opening of the blade holder, said blade holder is configured according to the invention in such a way that the blade can be removed from the blade holder or can be replaced in it exclusively when the blade is in an change-over position that extends beyond the working position of the blade in the distal direction. In this way any unintended release of the blade can be ruled out.

With a practical embodiment for configuring the blade holder it is proposed that the blade holder should be configured as a jaw-type flap mechanism. This structure constitutes a simple and safe container because the is clamped firmly in place between the jaw members. It is also advantageous if the blade holder is configured so that the incision depth of the blade can be adjusted by the arrangement of the blade in the blade holder. For this purpose various graduated contact surfaces or the like, for instance, can be configured in the blade holder to allow for exact adjustment of the incision depth by corresponding positioning of the blade.

To configure the blood sampling apparatus, it is proposed with the invention that said apparatus should be configured as a capillary tubule that can be detachably secured on the shaft.

Finally, it is proposed with the invention that a light conductor extending as far as the distal end of the shaft should be positioned in the shaft in order to ensure sufficient illumination of the working area even in spatially cramped conditions.

Additional characteristics and advantages of the invention can be seen from the appended illustrations, in which two embodiments of an inventive apparatus for fetal scalp blood removal are presented in schematic form, without restricting the invention to these embodiments.

BRIEF DESCRIPTION OF THE DRAWINGS

FIG. 1b shows a section along the line 1b-1b in FIG. 1a.

FIG. 1c shows an overhead view of the apparatus in FIG. 1a.

FIG. 2b shows an overhead view of the apparatus in FIG. 2a.

FIG. 3a shows a side view of an inventive apparatus for fetal scalp blood sampling, with the blade in change-over position.

FIG. 3b shows an overhead view of the apparatus in FIG. 3a.

DETAILED DESCRIPTION OF THE INVENTION

The apparatus for fetal scalp blood sampling schematically illustrated in FIGS. 1 through 3b consists essentially of a tubular-shaped shaft 1, a blade 2 that can be slid in the axial direction of the shaft 1 and that is mounted in the distal end of the shaft 1, and a blood collection device 3 positioned on the distal end of the shaft 1.

Figure 1A:
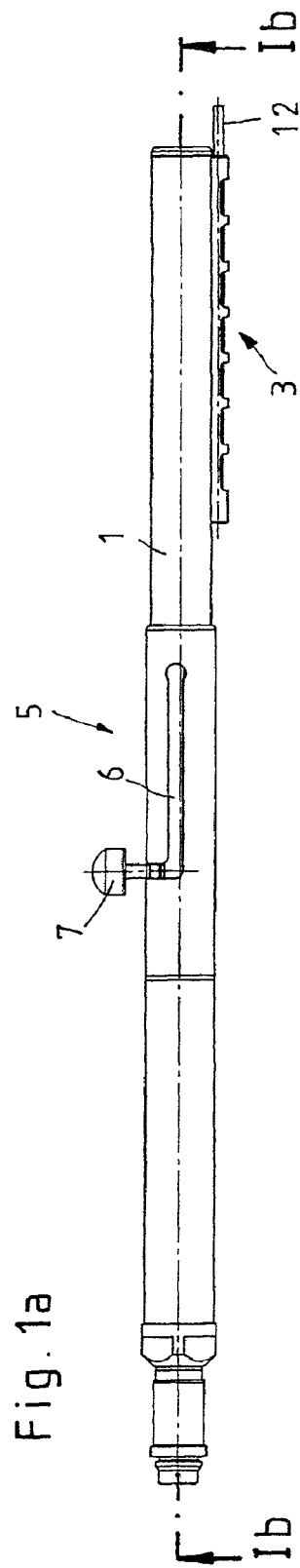
FIG. 1a shows a side view of a first embodiment of an inventive apparatus for fetal scalp blood removal, showing the blade in starting position.
Figure 1B:
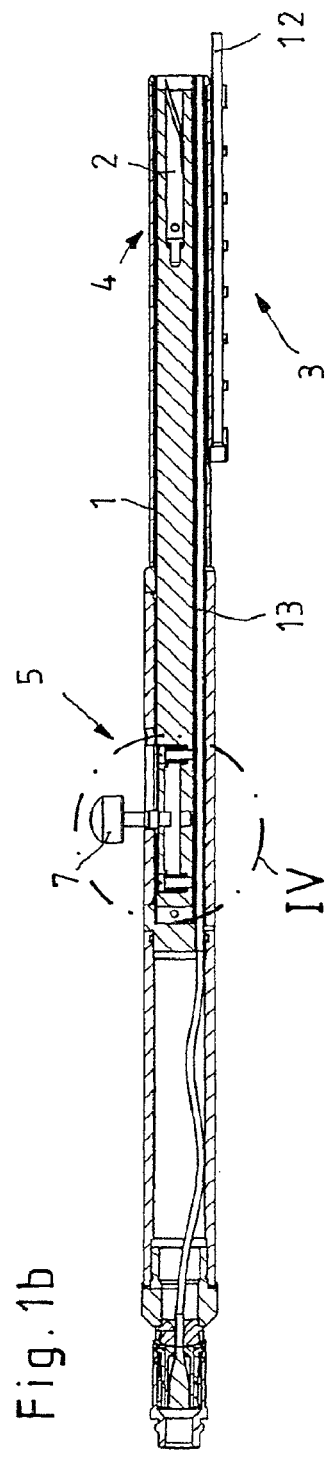

As can be seen in FIGS. 1b, 3a, and 3b, the blade 2 is replaceably mounted in a blade holder 4, which is mounted in the shaft 1 so that it can slide by means of a positioning mechanism 5 in the axial direction of the shaft 1. In the illustrated embodiment, the blade holder 4 is configured in jaw-like shape in such a way that the distal end of the blade holder 4 comprises a rigid base body 4a that contains and stores the blade 2 as well as a cap 4b that can be rotated with respect to the rigid base body 4a.

Figure 2A:
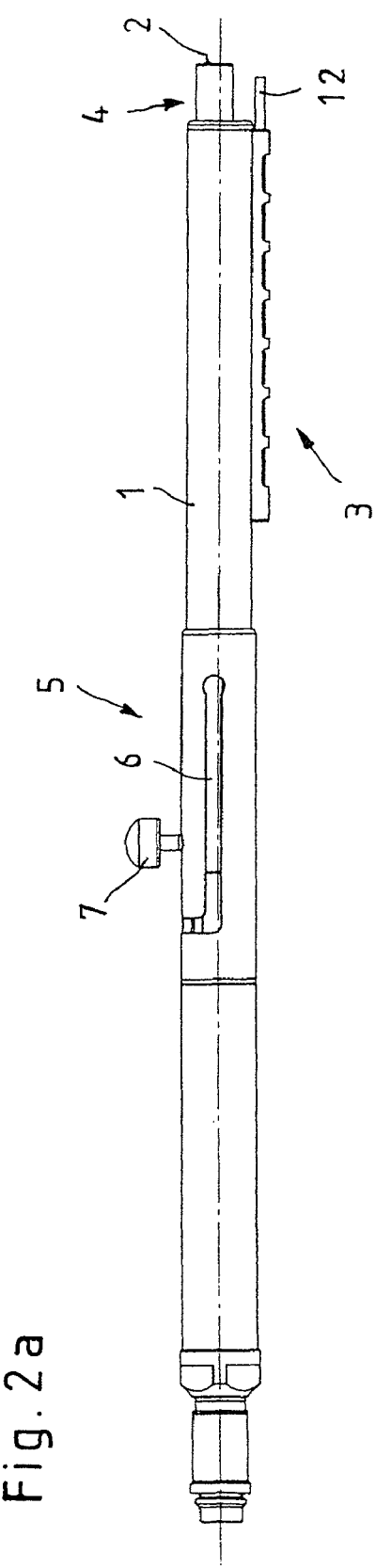
FIG. 2a shows a side view of an inventive apparatus for fetal scalp blood sampling, showing the blade in working position.
Figure 2B:
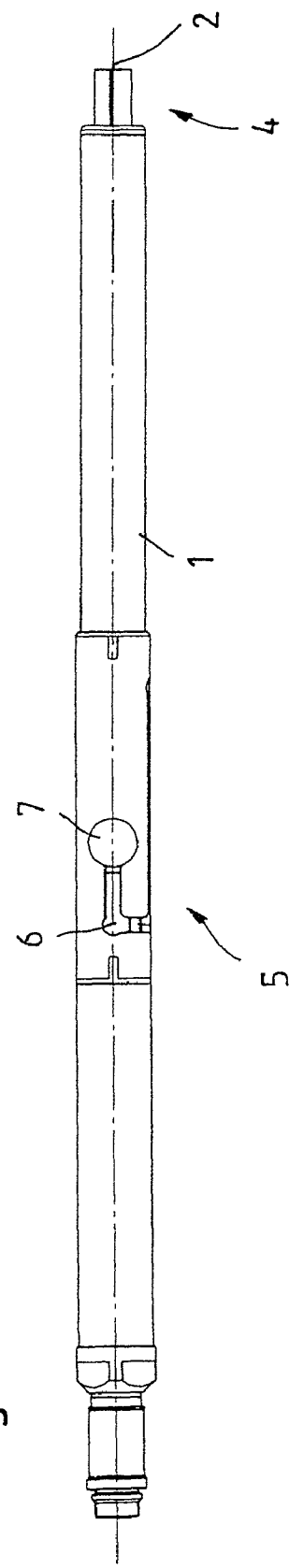

In the change-over position shown in FIG. 3a the blade holder 4 has been pushed by means of the positioning mechanism 5 out of the shaft 1 on the distal side until the cap 4b of the blade holder 4 can be flapped out from the rigid base body 4a in order to remove an old blade 2 and to position a new blade 2 in the blade holder 4. As can be seen in FIGS. 1b, 2a, 2b, as well as 3a and 3b, the blade 2 is always positioned in the blade holder 4 in such a way that the distal point of the blade 2 extends beyond the distal end of the blade holder 4.

The distance by which the blade 2 extends beyond the distal end of the blade holder 4 corresponds to the depth of incision of the blade 2 during removal of blood. The protrusion of the blade 2 and thus the incision depth of the blade can be adjusted by corresponding positioning of the blade 2 in the blade holder 4 by means of stops in the blade holder 4.

The positioning mechanism 5, by which the blade holder 4 equipped with the blade 2 can be slid in the axial direction of the shaft 1 inside the shaft 1, consists in the illustrated embodiment of a push-button 7 that can be slid in a guide track 6 configured in the shaft 1. As can be seen by juxtaposing the side views and overhead views of FIGS. 1a and 1c, 2a and 2b, and 3a and 3b, the guide track 6 is essentially of U-shaped configuration with two limbs running parallel in the axial direction of the shaft 1, so that the open diameter of the guide track 6 is of enlarged configuration at three points, that is, first at the two free ends, which are distal with respect to the entire instrument, of the parallel limbs of the U-shaped guide track 6, and then at a bend in the transition from the perpendicular base of the U-shaped guide track 6 to one limb.

These three positions with enlarged guide track diameter mark end positions of the blade holder 4 and thus of the blade 2 with respect to its position to the shaft 1.

Figure 1C:
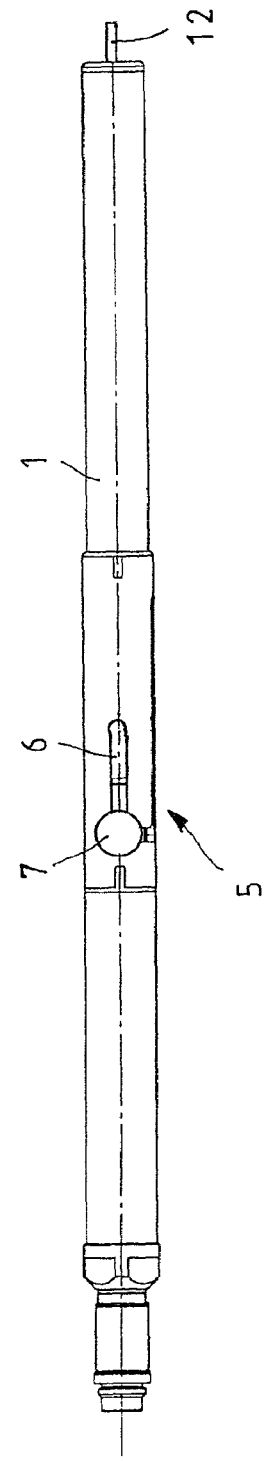

In the starting position shown in FIGS. 1a through 1c, the blade holder 4 is inserted by means of the positioning mechanism 5 into the shaft 1 until the blade 2 is completely inside the shaft 1 and no risk of injury can result from the blade 2 protruding on the distal side beyond the blade holder 4. The corresponding end position of the push-button 7 is the position in the transition from the perpendicular base of the U-shaped guide track 6 to one limb, that is the position of the push-button 7 mounted farthest from the proximal end of the shaft 1.

To be able to conduct the blade holder 4 by axial pushing, on the one hand, into the working position and, on the other hand, into the change-over position, the two parallel limbs of the U-shaped guide track 6 are configured with differing lengths.

The blade holder 4 is conducted into the working position by pushing the push-button 7 to the end of the short limb. In this position the blade holder 4 and the point of the blade 2 protrude beyond the distal end of the shaft 1 far enough so that pressing the apparatus against the head skin of the patient leads to insertion of the blade point into the head skin.

The change-over position shown in FIGS. 3a and 3b, in which the push-button 7 of the positioning mechanism 5 is found at the end of the long limb of the U-shaped guide track 6, differentiates itself from the working position in that the blade holder 4 has clearly been pushed out of the distal end of the shaft 1 by means of the positioning mechanism 5 through the working position until the cap 4b of the blade holder 4 can be opened to replace the blade 2.

To ensure that the blade holder 4 and thus also the blade 2 are secured in the particular end position and the push-button 7 cannot be pushed accidentally, the contours of the guide track 6 and of the push-button shaft are attuned to one another in such a way that the push-button 7 is positioned in the guide track 6 so that it cannot slide in the various end positions of the blade holder 4. For this purpose the shaft of the push-button 7 comprises a thickening, which corresponds exactly with the thickening of the guide track diameter in the area of the end positions. In this position, in which the thickened area of the push-button shaft is inserted in the enlarged guide track diameter, mere lateral pushing of the push-button 7 is no longer possible.

An additional pushing of the push-button 7 is possible only when the push-button is pressed downward inside the guide track 6 until the thickened area moves out of engagement with the guide track 6.

Unintentional actuation of the positioning mechanism 5 is further prevented in that the push-button 7 can be pressed against the force of at least one spring-elastic element 8 into the guide track 6. This spring force acting on the push-button 6 thus, on the one hand, prevents an unintentional pushing of the push-button 6 by lateral impact and, on the other hand, ensures that the push-button 6 is pre-tensed in the individual slide-proof end positions.

Figure 4:
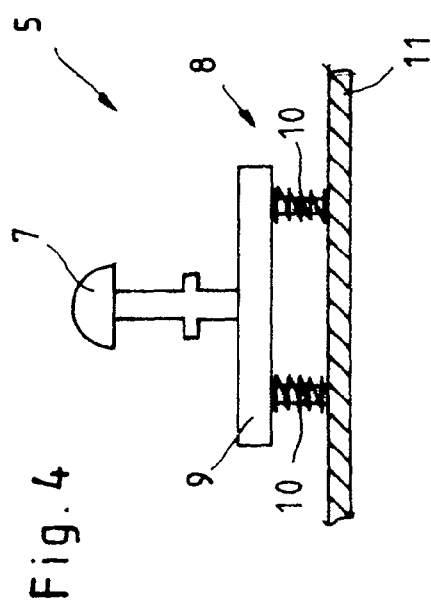
FIG. 4 shows an enlarged close-up view of detail IV from FIG. 1b.

As can be seen from FIG. 4, the spring-elastic element 8 that pre-tenses the push-button 6 is configured in the illustrated embodiment in such a way that the shaft of the push-button 6 is positioned on a base plate 9, which is supported by two spring elements 10 on a push-pull rod 11 of the positioning mechanism 5.

As can further be seen in particular from the side views in FIGS. 1a, 2a, and 3a, the blood collecting apparatus 3 in the illustrated embodiment consists of a capillary tubule 12 that can be exchangeably secured laterally on the distal end of the shaft 1 and that imbibes the blood sample by capillary action.

To ensure, even under spatially cramped conditions, that there is sufficient illumination of the operating area at all times, a light conductor 13 is positioned as well in the shaft 1, said conductor extending as far as the distal end and illuminating the operating area in the immediate vicinity of both the blade 2 and the capillary tubule.

Figure 5:
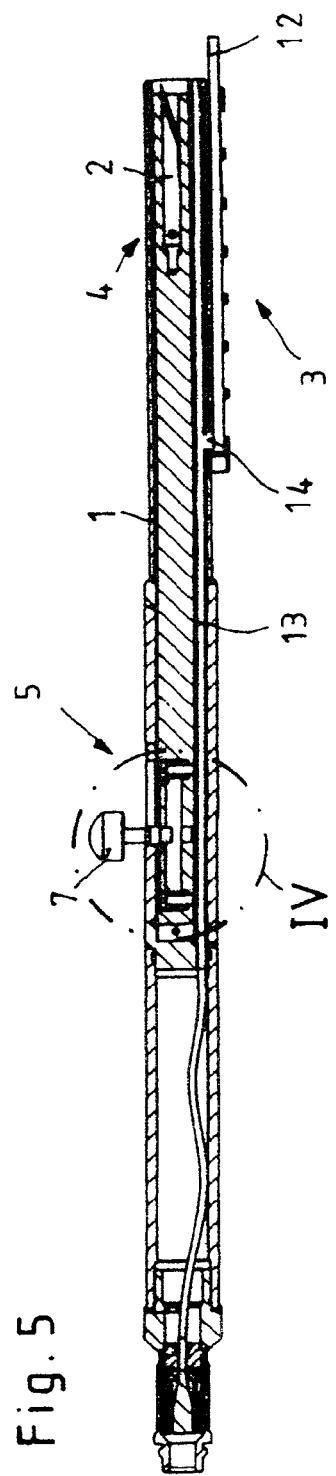
FIG. 5 shows a sectional view corresponding to FIG. 1b but showing a second embodiment of an inventive apparatus for fetal scalp blood sampling.

The second embodiment of the apparatus for fetal scalp blood sampling, illustrated in FIG. 5, is distinguished from the previously described embodiment in that the same light conductor 13 or an additional light conductor 13 comprises a light emission aperture 14, by which the proximal end of the capillary tubule 12 can also be illuminated. This additional illumination of the proximal end of the capillary tubule 12 is advantageous for the user because in this way the operator can determine whether an amount of blood sufficient for the following examinations has been incorporated into the capillary tubule 12 on the strength of the active capillary forces.

An apparatus of this configuration for fetal scalp blood sampling is distinguished in that the apparatus is configured as a reusable instrument because of the replaceability of the blade 2.

For this purpose the apparatus should of course be configured with corresponding choice of materials and insulating measures so that the apparatus can be completely dismantled and autoclaved for cleaning purposes.

An additional advantage of the present apparatus consists in the fact that the blade 2 can be converted by means of the positioning mechanism 5 into defined and fixable end positions that ensure a high degree of operating safety.

What is claimed is:

1. An apparatus for fetal scalp blood sampling, having a shaft, a blade that is mounted removably in the distal end of the shaft and that is mounted in a blade holder that can be slid in the axial direction of the shaft by means of a positioning mechanism comprising a guide track between a starting position mounted in the shaft, a working position extending beyond the distal end of the shaft and a change-over position protruding beyond the working position in the distal direction of the shaft, wherein the blade is fixed in place by the positioning mechanism in each particular end position, and also having a blood sampling device mounted on the distal end of the shaft, characterized in that the positioning mechanism includes a spring loaded push-button which can be pressed down into the guide track in a direction perpendicular to the sliding direction against the force of a least one spring element and that can be slid in the guide track between the end positions, wherein the guide track is shaped as a single U with both limbs of the U-shaped guide track running parallel in the axial direction of the shaft having differing lengths, and in that in the change-over position of the blade holder the blade can be removed directly without taking apart any further component of the apparatus.

2. The apparatus according to claim 1, characterized in that the contours of the guide track and of the push-button shaft are adapted to one another in such a way that the push-button is positioned in the guide track so that it cannot slide in the various end positions of the blade.

3. The apparatus according to claim 1, characterized in that the blade can be removed from or inserted into the blade holder exclusively in the change-over position.

4. The apparatus according to claim 1, characterized in that the blade holder is configured as a jaw-like flapping mechanism.

5. The apparatus according to claim 1, characterized in that the incision depth of the blade can be adjusted by the position of the blade in the blade holder.

6. The apparatus according to claim 1, characterized in that the blood sampling apparatus is configured as a capillary tubule that can be exchangeably secured on the shaft.

7. The apparatus according to claim 1, characterized in that a light conductor is positioned in the shaft extending to the distal end of the shaft.

* * * * *